United States Patent
Kariyazono et al.

(10) Patent No.: US 9,902,708 B2
(45) Date of Patent: Feb. 27, 2018

(54) CYCLIC COMPOUND AND OPTICAL MATERIAL COMPOSITION INCLUDING SAME

(71) Applicant: MITSUBISHI GAS CHEMICAL COMPANY, INC., Tokyo (JP)

(72) Inventors: Kazuki Kariyazono, Osaka (JP); Takashi Aoki, Osaka (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 0 days.

(21) Appl. No.: 15/532,295

(22) PCT Filed: Mar. 1, 2016

(86) PCT No.: PCT/JP2016/056151
§ 371 (c)(1),
(2) Date: Jun. 1, 2017

(87) PCT Pub. No.: WO2016/158155
PCT Pub. Date: Oct. 6, 2016

(65) Prior Publication Data
US 2017/0334876 A1      Nov. 23, 2017

(30) Foreign Application Priority Data

Mar. 27, 2015   (JP) ................................ 2015-065894

(51) Int. Cl.
| C07D 327/02 | (2006.01) |
| C07D 331/02 | (2006.01) |
| C08G 75/08 | (2006.01) |
| G02B 1/04 | (2006.01) |

(52) U.S. Cl.
CPC ......... *C07D 327/02* (2013.01); *C07D 331/02* (2013.01); *C08G 75/08* (2013.01); *G02B 1/041* (2013.01)

(58) Field of Classification Search
CPC .................................................. C07D 327/02
USPC ....................................................... 528/380
See application file for complete search history.

(56) References Cited

U.S. PATENT DOCUMENTS

| 5,446,173 A | 8/1995 | Kanesaki et al. |
| 5,484,872 A | 1/1996 | Kanesaki et al. |
| 6,117,923 A | 9/2000 | Amagai et al. |
| 6,472,495 B1 | 10/2002 | Yoshimura et al. |
| 8,362,169 B2 * | 1/2013 | Nakayama ........... C07D 319/12 526/257 |
| 2003/0204030 A1* | 10/2003 | Higuchi ............ C08G 63/6886 525/535 |
| 2004/0122201 A1 | 6/2004 | Yoshimura et al. |
| 2010/0331508 A1* | 12/2010 | Sato ..................... C07D 327/06 526/257 |

FOREIGN PATENT DOCUMENTS

| JP | 6-16657 | 1/1994 |
| JP | 9-110979 | 4/1997 |
| JP | 10-298287 | 11/1998 |
| JP | 2001-2783 | 1/2001 |
| JP | 2001-31675 | 2/2001 |
| JP | 2001-131257 | 5/2001 |
| JP | 2002-122701 | 4/2002 |
| JP | 2004-137481 | 5/2004 |
| WO | 02/072670 | 9/2002 |

OTHER PUBLICATIONS

International Search Report issued in Patent Application No. PCT/JP2016/056151, dated May 31, 2016.

* cited by examiner

*Primary Examiner* — Michael M Dollinger
(74) *Attorney, Agent, or Firm* — Greenblum & Bernstein, P.L.C.

(57) ABSTRACT

One embodiment of the present invention can provide an optical material composition that includes a cyclic compound that is represented by formula (1) and an episulfide that is represented by formula (2). Another embodiment of the present invention can provide an optical material production method that includes a step wherein, with respect to the total amount of the optical material composition, 0.0001-10 mass % of a polymerization catalyst is added to the optical material composition and the optical material composition is polymerization cured. (In formula (2), m is an integer from 0 to 4, and n is an integer from 0 to 2.)

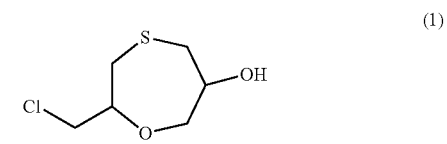

(1)

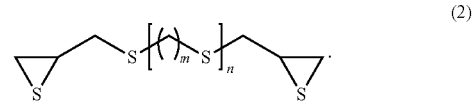

(2)

13 Claims, No Drawings

CYCLIC COMPOUND AND OPTICAL MATERIAL COMPOSITION INCLUDING SAME

TECHNICAL FIELD

The present invention relates to a novel cyclic compound and an optical material composition containing the same. More particularly, the present invention relates to a novel cyclic compound and an optical material composition containing the same that can favorably be used in optical materials, for example, for a plastic lens, a prism, optical fiber, an information storage board, a filter and the like, in particular, a plastic lens.

BACKGROUND ART

A plastic lens is light in weight, has excellent toughness, and can easily be dyed. Properties that are particularly required for a plastic lens include low density, high transparency, reduced yellowness, optical properties such as high refractive index, high Abbe's number, high heat resistance and high strength. A high refractive index allows thinning of the lens while a high Abbe's number reduces chromatic aberration of the lens.

Recently, a number of examples using an organic compound having a sulfur atom have been reported for the purpose of achieving a high refractive index and a high Abbe's number. Among them, a polyepisulfide compound having a sulfur atom is known to have good balance between the refractive index and the Abbe's number (Patent document 1). Moreover, since polyepisulfide compounds can react with various compounds, their compositions with various compounds such as thiourethane have been proposed for enhancing physical properties (Patent documents 2-5). In addition, as a composition comprising a polyepisulfide compound, an optical material containing an inorganic compound having a sulfur atom and/or a selenium atom has been proposed with the aim of achieving a higher refractive index (Patent document 6).

PRIOR ART DOCUMENTS

Patent Documents

Patent document 1: Japanese Unexamined Patent Application Publication No. H09-110979
Patent document 2: Japanese Unexamined Patent Application Publication No. H10-298287
Patent document 3: Japanese Unexamined Patent Application Publication No. 2001-002783
Patent document 4: Japanese Unexamined Patent Application Publication No. 2001-131257
Patent document 5: Japanese Unexamined Patent Application Publication No. 2002-122701
Patent document 6: Japanese Unexamined Patent Application Publication No. 2004-137481

SUMMARY OF INVENTION

Problem to be Solved by Invention

The above-described productions of optical materials, in particular plastic lenses for spectacles, however, were sometimes associated with reduction in yield due to a defect caused by a peeling mark remaining on the polymerized/cured lens after mold release or due to a mold release failure.

The defect caused by the remaining peeling mark refers to a defect where a peeling mark remains on the lens upon mold release after polymerization/curing, which renders the lens unusable. The defect of remaining peeling mark is especially significant in negative lenses with higher power, and improvement has been required. The mold release failure means poor releasability and refers to a defect that causes lens chipping upon releasing the lens from the mold, which renders the lens unusable. The mold release failure is especially significant in positive lenses with higher power, and improvement has been required.

These defects conflict with each other, where usually good peeling tends to result poor releasability while good releasability tends to result poor peeling. Therefore, a method for controlling and improving these defects at the same time has been demanded.

The present invention has an objective of providing a compound which can improve reduction in yield due to the defect of a remaining peeling mark or the mold release failure of the lens, an optical material composition containing said compound and an episulfide compound, an optical material, an optical lens, and a method for producing the same.

Means for Solving Problem

The present inventors have gone through keen studies in view of the above-described circumstances, and as a result of which found that the above-described problems can be solved with an optical material composition containing a specific compound and an episulfide compound, thereby accomplishing the present invention.

Thus, the present invention is as follows.
<1> A cyclic compound represented by Formula (1) below:

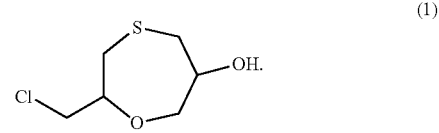

<2> A composition for optical material comprising the cyclic compound represented by Formula (1) according to <1> and an episulfide compound represented by Formula (2) below:

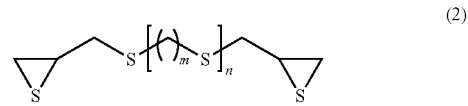

wherein m represents an integer of 0-4 and n represents an integer of 0-2.
<3> The composition for optical material according to <2>, wherein the amount of the cyclic compound represented by Formula (1) above is 0.001-5.0% by mass.
<4> The composition for optical material according to <2> or <3>, further comprising polythiol.
<5> The composition for optical material according to any one of <2> to <4>, further comprising inorganic sulfur.
<6> The composition for optical material according to <4> or <5>, further comprising polyisocyanate.
<7> A polymerizable/curable composition comprising the composition for optical material according to any one of <2> to <6> and a polymerization catalyst at 0.0001% by mass to 10% by mass with respect to the total amount of the composition for optical material.

<8> An optical material obtained by curing the composition for optical material according to any one of <2> to <6> or the polymerizable/curable composition according to <7>.

<9> An optical lens comprising the optical material according to <8>.

<10> A method for producing an optical material, comprising the steps of: adding a polymerization catalyst at 0.0001% by mass to 10% by mass with respect to the total amount of the composition for optical material according to any one of <2> to <6>; and polymerizing/curing the resultant.

<11> The method for producing an optical material according to <10>, further comprising a step of allowing partial polymerization of the episulfide compound represented by Formula (2) and sulfur, prior to the polymerization/curing step.

Effects of Invention

According to the present invention, an optical material, for example, for a plastic lens, can be produced in an industrially efficient manner while suppressing a peeling defect and a mold release failure caused upon polymerizing/curing a composition containing an episulfide compound at the same time, by adding a cyclic compound represented by Formula (1). Moreover, addition of the cyclic compound represented by Formula (1) also allows suppression of viscosity variation in the episulfide compound during storage, thereby stabilizing production conditions.

EMBODIMENTS FOR CARRYING OUT INVENTION

Hereinafter, the present invention will be described in detail.

The present invention is a cyclic compound represented by Formula (1) above, and an optical material composition comprising the cyclic compound represented by Formula (1) above and a polymerizable compound. While examples of the polymerizable compound include an episulfide compound, a vinyl compound, a methacrylic compound, an acrylic compound and an allyl compound, it is preferably an episulfide compound, and more preferably an episulfide compound represented by Formula (2) above.

The proportion of the cyclic compound represented by Formula (1) above in the optical material composition of the present invention is preferably 0.001-5.0% by mass, more preferably 0.005-3.0% by mass and particularly preferably 0.01-2.0% by mass. If the cyclic compound represented by Formula (1) exceeds 5.0% by mass, heat resistance and light resistance may be deteriorated and a mold release failure may occur, which may cause an adverse effect on productivity of the optical material. On the other hand, if the cyclic compound represented by Formula (1) is less than 0.001% by mass, a peeling defect occurs, which may cause an adverse effect on productivity of the optical material.

In addition, the proportion of the episulfide compound represented by Formula (2) above in the optical material composition is preferably 40-99.99% by mass, more preferably 50-99.99% by mass and particularly preferably 60-99.99% by mass.

Hereinafter, the cyclic compound represented by Formula (1) above will be described in detail.

Hereinafter, a method for producing a cyclic compound represented by Formula (1) of the present invention will be described although the production method is not particularly limited thereto.

According to a method for producing a cyclic compound represented by Formula (1) of the present invention: hydrogen sulfide is reacted with epichlorohydrin to obtain a compound represented by Formula (3) below; the resulting compound represented by Formula (3) is reacted with alkali in an alcohol solvent to allow an intramolecular dehydrohalogenation reaction to proceed; and the resultant is subjected to acid treatment, thereby obtaining a cyclic compound represented by Formula (1) as a mixture with other closed-ring compound or the like. This crude product is extracted and washed with an organic solvent to separate and purify the compound of interest, thereby obtaining the cyclic compound represented by Formula (1).

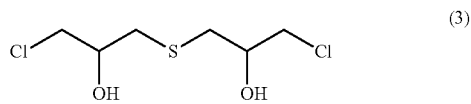 [SMILES: OC(CCl)CSCC(O)CCl]

(3)

A method for producing a compound represented by Formula (3) will be described specifically.

A compound represented by Formula (3) can be obtained through a reaction between hydrogen sulfide and epichlorohydrin.

Preferably, a catalyst is used upon reaction between epichlorohydrin and hydrogen sulfide. Examples of the catalyst include inorganic acids, organic acids, Lewis acid, silicic acid, boric acid, quaternary ammonium salts, inorganic bases and organic bases. It is preferably an organic acid, a quaternary ammonium salt or an inorganic bases and more preferably a quaternary ammonium salt or an inorganic base. Specific examples include tetramethylammonium chloride, tetramethylammonium bromide, tetramethylammonium acetate, tetraethylammonium chloride, tetraethylammonium bromide, tetraethylammonium acetate, tetrabutylammonium chloride, tetrabutylammonium bromide, tetrabutylammonium acetate, tetrahexylammonium chloride, tetrahexylammonium bromide, tetrahexylammonium acetate, tetraoctylammonium chloride, tetraoctylammonium bromide, tetraoctylammonium acetate, sodium hydroxide, potassium hydroxide, magnesium hydroxide and calcium hydroxide. Among them, sodium hydroxide, potassium hydroxide, and calcium hydroxide are preferable.

While the amount of the catalyst added is not particularly limited as long as it allows the reaction to proceed, the amount used is preferably 0.00001-0.5 mol and more preferably 0.001-0.1 mol per 1 mol of epichlorohydrin. If the amount of the catalyst is less than 0.00001 mol, the reaction may not proceed or become slower which is unfavorable and if the amount of the catalyst exceeds 0.5 mol, the reaction may proceed too much which renders control of the reaction difficult.

While the ratio of epichlorohydrin and hydrogen sulfide is not particularly limited as long as the reaction proceeds, the molar ratio of epichlorohydrin to hydrogen sulfide (epichlorohydrin/hydrogen sulfide) is preferably 0.6-8, more preferably 0.8-6 and still more preferably 1.0-4. If the molar ratio is less than 0.6 or exceeds 8, the amount of the unreacted raw material becomes excessive, which is economically unfavorable.

While a solvent may or may not be used, the solvent, if used, may be water, an alcohol, an ether, a ketone, an aromatic hydrocarbon or a halogenated hydrocarbon. Specific examples include water, methanol, ethanol, propanol, isopropanol, ethylene glycol, diethyl ether, tetrahydrofuran, dioxane, methyl cellosolve, ethyl cellosolve, butyl cellosolve, methyl ethyl ketone, acetone, benzene, toluene, xylene, dichloroethane, chloroform and chlorobenzene. Among them, it is preferably water, methanol or toluene, and particularly preferably water or methanol.

While the reaction temperature is not particularly limited as long the reaction proceeds, it is carried out preferably at −10° C.-80° C., more preferably at 5° C.-50° C. and still more preferably at 10° C.-40° C. While the reaction time is not particularly limited, it is usually less than 20 hours. If the temperature is lower than −10° C., the reaction may not proceed or become slower which is unfavorable and if the temperature exceeds 80° C., oligomerization occurs which results a high molecular weight which is unfavorable.

Subsequently, a method for producing a cyclic compound represented by Formula (1) will be described.

A compound represented by Formula (3) is reacted with alkali and then the resultant is subjected to acid treatment, thereby obtaining a cyclic compound represented by Formula (1) as a mixture with other byproduct.

Specific examples of alkali that is to be reacted with the compound represented by Formula (3) include hydroxides of ammonia, alkali metals and alkali earth metals, carbonates of alkali metals and alkali earth metals, hydrogen carbonates of alkali metals, and ammonium salts of alkali metals and alkali earth metals. These may be used in a form of an aqueous solution. The alkali is preferably sodium hydroxide, potassium hydroxide, calcium hydroxide, sodium carbonate, potassium carbonate, ammonium carbonate, sodium hydrogen carbonate or potassium hydrogen carbonate, and more preferably, sodium hydroxide or potassium hydroxide.

While the amount of the alkali used cannot be defined unconditionally, usually 0.20-2.0, preferably 0.50-1.5 and more preferably 0.70-1.0 equivalents of alkali is used to the equivalent of the compound represented by Formula (3). A small or large amount of alkali results in reduction in yield.

A solvent is preferably used upon reaction. In this case, the solvent used is not particularly limited and any solvent may be used, but it is preferably water, an alcohol, an ether, a ketone, an aliphatic hydrocarbon, an aromatic hydrocarbon or a halogenated hydrocarbon. These may be used alone or used as a mixture. Specific examples of the alcohol include methanol, ethanol, propanol, isopropanol and ethylene glycol; specific examples of the ether include diethyl ether, tetrahydrofuran and dioxane; specific examples of the ketone include methyl cellosolve, ethyl cellosolve, butyl cellosolve, methyl ethyl ketone and acetone; specific examples of the aliphatic hydrocarbon include hexane, heptane and octane; specific examples of the aromatic hydrocarbon include benzene, toluene and xylene; and specific examples of the halogenated hydrocarbon include dichloroethane, chloroform and chlorobenzene. More preferably, the solvent is water or an alcohol, specific examples being water, methanol, propanol and isopropanol. Particularly preferably, the solvent is methanol.

While the amount of the solvent is not particularly limited, it is usually 10-10000 parts by mass, preferably 100-5000 parts by mass and more preferably 500-1000 parts by mass to 100 parts by mass of the compound represented by Formula (3).

The reaction temperature is preferably −5° C. or lower, more preferably −10° C. or lower and still more preferably −15° C. or lower. The reaction time is not particularly limited. A high reaction temperature lowers reaction selectivity to the cyclic compound represented by Formula (1) and reduces yield of the cyclic compound represented by Formula (1).

In addition, the compound represented by Formula (3) may be dropped into a mixed solvent of an aqueous solution of an organic solvent and a basic compound to allow reaction.

Furthermore, an acid is added to the resulting reaction solution to allow reaction, and then an organic solvent is added for extraction, thereby obtaining a crude product containing the cyclic compound represented by Formula (1). While the acid is not particularly limited and any acid may be used, it is preferably sulfuric acid, hydrochloric acid, nitric acid and acetic acid, and more preferably sulfuric acid and hydrochloric acid. This crude product is washed with water, and purified by distillation, column purification or the like, thereby obtaining the cyclic compound represented by Formula (1).

The optical material composition of the present invention is characterized by comprising the cyclic compound represented by Formula (1) above, where a predetermined amount of the cyclic compound represented by Formula (1) above is preferably added to the above-described episulfide compound represented by Formula (2) as a polymerizable compound in advance. By adding the cyclic compound represented by Formula (1) above to the episulfide compound represented by Formula (2) before storing the resultant, viscosity variation during storage can be suppressed, and thus production conditions of the optical material can be stabilized.

In the optical material composition of the present invention, the episulfide compound represented by Formula (2) may be used as the polymerizable compound. Specific examples of the episulfide compound represented by Formula (2) include episulfides such as bis(β-epithiopropyl)sulfide, bis(β-epithiopropyl)disulfide, bis(β-epithiopropyl thio)methane, 1,2-bis(β-epithiopropyl thio)ethane, 1,3-bis(β-epithiopropyl thio)propane and 1,4-bis(β-epithiopropyl thio)butane. The episulfide compound represented by Formula (2) may be used alone or two or more types of them may be used as a mixture.

Among them, a preferable compound is bis(β-epithiopropyl)sulfide (in Formula (2), n=0) or bis(β-epithiopropyl)disulfide (in Formula (2), m=0 and n=1), and the most preferable compound is bis(β-epithiopropyl)sulfide (in Formula (2), n=0).

The optical material composition of the present invention may contain a polythiol compound as a polymerizable compound in order to improve the color tone of the resulting resin upon heating. The content of the polythiol compound is usually 1-25% by mass, preferably 2-25% by mass and particularly preferably 5-20% by mass, provided that the total of the optical material composition is 100% by mass. If the content of the polythiol compound is less than 1% by mass, yellowing may be caused upon molding a lens and if the content exceeds 25% by mass or less, heat resistance may be deteriorated. The polythiol compound may be used alone or two or more of them may be used as a mixture for the present invention.

Specific examples of the polythiol compound include methanedithiol, methanetrithiol, 1,2-dimercaptoethane, 1,2-dimercaptopropane, 1,3-dimercaptopropane, 2,2-dimercaptopropane, 1,4-dimercaptobutane, 1,6-dimercaptohexane, bis(2-mercaptoethyl)ether, bis(2-mercaptoethyl)sulfide, 1,2-bis(2-mercaptoethyloxy)ethane, 1,2-bis(2-mercaptoethyl thio)ethane, 2,3-dimercapto-1-propanol, 1,3-dimercapto-2-propanol, 1,2,3-trimercaptopropane, 2-mercaptomethyl-1,3-dimercaptopropane, 2-mercaptomethyl-1,4-dimercaptobutane, 2-(2-mercaptoethyl thio)-1,3-dimercaptopropane, 4-mercaptomethyl-1,8-dimercapto-3,6-dithiaoctane, 2,4-dimercaptomethyl-1,5-dimercapto-3-thiapentane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1-tris(mercaptomethyl)propane, tetrakis(mercaptomethyl)methane, ethylene glycol bis(2-mercaptoacetate), ethylene glycol bis(3-mercaptopropionate), diethylene glycol bis(2-mercaptoacetate), diethylene glycol bis(3-mercaptopropionate), 1,4-butanediol bis(2-mercaptoacetate), 1,4-butanediol bis(3-mercaptopropionate), trimethylolpropane tristhioglycolate, trimethylolpropane trismercaptopropionate, pentaerythritol tetrakis thioglycolate, pentaerythritol tetrakis mercaptopropionate, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl)cyclohexane, 2,5-dimercaptomethyl-1,4-dithiane, 2,5-dimercaptomethyl-1,4-dithiane, 2,5-bis(2-mercaptoethyl thiomethyl)-1,4-dithiane, 2,5-dimercaptomethyl-1-thiane, 2,5-dimercaptoethyl-1-thiane, 2,5-dimercaptomethyl thiophene, 1,2-dimercaptobenzene, 1,3-dimercaptobenzene, 1,4-dimercaptobenzene, 1,3-bis(mercaptomethyl)benzene, 1,4-bis(mercaptomethyl)benzene, 2,2'-dimercaptobiphenyl, 4,4'-dimercaptobiphenyl, bis(4-mercaptophenyl)methane, 2,2-bis(4-mercaptophenyl)propane, bis(4-mercaptophenyl)ether, bis(4-mercaptophenyl)sulfide, bis(4-mercaptophenyl)sulfone, bis(4-mercaptomethylphenyl)methane, 2,2-bis(4-mercaptomethylphenyl)propane, bis(4-mercaptomethylphenyl)ether, bis(4-mercaptomethylphenyl)sulfide, 2,5-dimercapto-1,3,4-thiadiazole, 3,4-thiophenedithiol, and 1,1,3,3-tetrakis(mercaptomethyl thio)propane.

Among them, specifically preferable examples are bis(2-mercaptoethyl)sulfide, 2,5-dimercaptomethyl-1,4-dithiane, 1,3-bis(mercaptomethyl)benzene, 1,4-bis(mercaptomethyl)benzene, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethyl thio)propane, pentaerythritol tetrakis mercaptopropionate, pentaerythritol tetrakis thioglycolate, trimethylolpropane tristhioglycolate and trimethylolpropane trismercaptopropionate, more preferable examples are bis(2-mercaptoethyl)sulfide, 2,5-bis(2-mercaptomethyl)-1,4-dithiane, 4-mercaptomethyl-1,8-dimercapto-3,6-dithiaoctane, 1,3-bis(mercaptomethyl)benzene, pentaerythritol tetrakis mercaptopropionate and pentaerythritol tetrakis thioglycolate, and particularly preferable compounds are bis(2-mercaptoethyl)sulfide, 2,5-dimercaptomethyl-1,4-dithiane and 4-mercaptomethyl-1,8-dimercapto-3,6-dithiaoctane.

The optical material composition of the present invention may contain sulfur. The amount of sulfur used is usually 0.1-40 parts by mass, preferably 0.5-30 parts by mass and particularly preferably 1-25 parts by mass, provided that the total amount of the optical material composition is 100 parts by mass.

Sulfur used for the present invention may take any form. Specifically, sulfur is fine powder sulfur, colloidal sulfur, precipitated sulfur, crystalline sulfur, sublimated sulfur or the like, and preferably fine powder sulfur with fine particles.

Sulfur used for the present invention may be produced by any method. The sulfur production method may employ purification from natural sulfur ore by sublimation, derivation of sulfur buried underground by solution mining, recovery using, as a raw material, hydrogen sulfide or the like obtained during petroleum or natural gas desulfurization, or else. Any production method can be employed.

Preferably, the particle size of sulfur used for the present invention is smaller than the mesh size of 10, namely, sulfur is fine powder finer than the mesh size of 10. If the particle size of sulfur is larger than the mesh size of 10, sulfur is difficult to be dissolved completely, in which case unfavorable reaction or the like may occur in the first step and cause defects. The particle size of sulfur is more preferably smaller than the mesh size of 30, and most preferably smaller than the mesh size of 60.

The purity of sulfur used for the present invention is preferably 98% or higher, more preferably 99.0% or higher, still more preferably 99.5% or higher and most preferably 99.9% or higher. If the purity of sulfur is 98% or higher, the color tone of the resulting optical material will be improved compared to a case where the purity is less than 98%.

If sulfur is to be used, sulfur is preferably preliminarily reacted with the episulfide compound so that sulfur is mixed homogeneously. Conditions for this preliminary polymerization reaction are preferably −10° C.-120° C. for 0.1-240 hours, more preferably 0-100° C. for 0.1-120 hours and particularly preferably 20-80° C. for 0.1-60 hours. A catalyst can effectively be used to allow the preliminary reaction to proceed, where preferable examples include 2-mercapto-1-methylimidazole, triphenylphosphine, 3,5-dimethylpyrazole, N-cyclohexyl-2-benzothiazolylsulfinamide, dipentamethylenethiuram tetrasulfide, tetrabutylthiuram disulfide, tetraethylthiuram disulfide, 1,2,3-triphenylguanidine, 1,3-diphenylguanidine, 1,1,3,3-tetramethyleneguanidine, aminoguanidine urea, trimethyl thiourea, tetraethyl thiourea, dimethylethyl thiourea, zinc dibutyldithiocarbamate, zinc dibenzyldithiocarbamate, zinc diethyldithiocarbamate, zinc dimethyldithiocarbamate and pipecolium pipecolyldithiocarbamate. Moreover, sulfur is used by this preliminary polymerization reaction for preferably 10% or higher (provided that sulfur before the reaction is 100%), and more preferably 20% or higher. The preliminary reaction may be carried out under any atmosphere such as an air atmosphere, in an inert gas such as nitrogen or in a closed condition under normal, increased or reduced pressure. Here, liquid chromatography or a refractometer may be used in order to detect the degree of progress of the preliminary reaction.

The optical material composition of the present invention may contain a polyisocyanate compound as the polymerizable compound in order to enhance the strength of the resulting resin. The content of the polyisocyanate compound is usually 1-25% by mass, preferably 2-25% by mass and particularly preferably 5-20% by mass, provided that the total of the optical material composition is 100% by mass. If the content of the polyisocyanate compound is less than 1% by mass, strength may be reduced and if the content exceeds 25% by mass or less, color tone may be deteriorated. The polyisocyanate compound may be used alone or two or more of them may be used as a mixture for the present invention.

Specific examples of the polyisocyanate compound include diethylene diisocyanate, tetramethylene diisocyanate, hexamethylene diisocyanate, trimethylhexamethylene diisocyanate, cyclohexane diisocyanate, 1,3-bis(methyl isocyanate)cyclohexane, 1,4-bis(methyl isocyanate)cyclohexane, isophorone diisocyanate, 2,6-bis(methyl isocyanate) decahydronaphthalene, lysine triisocyanate, tolylenediisocyanate, o-tolidine diisocyanate, diphenylmethane diisocyanate, diphenylether diisocyanate, 3-(2'-cyclohexyl isocyanate)propyl isocyanate, isopropylidene bis (cyclohexyl isocyanate), 2,2'-bis(4-isocyanatephenyl) propane, triphenylmethane triisocyanate, bis(diisocyanate tolyl)phenylmethane, 4,4',4''-triisocyanate-2,5-dimethoxy phenylamine, 3,3'-dimethoxy benzidine-4,4'-diisocyanate, 1,3-phenylene diisocyanate, 1,4-phenylene diisocyanate, 4,4'-diisocyanatebiphenyl, 4,4'-diisocyanate-3,3'-dimethylbiphenyl, dicyclohexylmethane-4,4'-diisocyanate, 1,1'-methylenebis(4-isocyanatebenzene), 1,1'-methylenebis(3-methyl-4-isocyanatebenzene), m-xylylene diisocyanate, p-xylylene diisocyanate, m-tetramethyl xylylene diisocyanate, p-tetramethyl xylylene diisocyanate, 1,3-bis(2-isocyanate-2-propyl)benzene, 2,6-bis(methyl isocyanate)naphthalene, 1,5-naphthalene diisocyanate, bis(methyl isocyanate) tetrahydrodicyclopentadiene, bis(methyl isocyanate) dicyclopentadiene, bis(methyl isocyanate) tetrahydrothiophene, bis(methyl isocyanate)norbornene, bis (methyl isocyanate)adamantane, thiodiethyl diisocyanate, thiodipropyl diisocyanate, thiodihexyl diisocyanate, bis[(4-methyl isocyanate)phenyl]sulfide, 2,5-diisocyanate-1,4-dithiane, 2,5-methyl diisocyanate-1,4-dithiane, 2,5-methyl diisocyanate thiophene, dithiodiethyl diisocyanate and dithiodipropyl diisocyanate.

The polyisocyanate compounds intended by the present invention, however, are not limited to these examples. Also, they may be used alone or two or more types of them may be used as a mixture.

Preferable specific examples among them are isophorone diisocyanate, tolylenediisocyanate, diphenylmethane diisocyanate, hexamethylene diisocyanate, m-xylylene diisocyanate, p-xylylene diisocyanate, m-tetramethyl xylylene diisocyanate, p-tetramethyl xylylene diisocyanate, 1,3-bis (methyl isocyanate)cyclohexane, 1,4-bis(methyl isocyanate) cyclohexane, bis(methyl isocyanate)norbornene and 2,5-methyl diisocyanate-1,4-dithiane, where preferable compounds among them are isophorone diisocyanate, tolylenediisocyanate, diphenylmethane diisocyanate, hexamethylene diisocyanate, 1,3-bis(methyl isocyanate)cyclohexane and m-xylylene diisocyanate, and particularly preferable compounds are isophorone diisocyanate, m-xylylene diisocyanate and 1,3-bis(methyl isocyanate)cyclohexane.

Furthermore, a proportion of the SH groups of the polythiol compound to the NCO groups of the polyisocyanate compound, that is, SH group/NCO group, is preferably 1.0-2.5, more preferably 1.25-2.25 and still more preferably 1.5-2.0. If the above-described proportion is less than 1.0, yellowing may be caused upon molding a lens and if the proportion exceeds 2.5, heat resistance may be deteriorated.

A polymerization catalyst is preferably added upon polymerizing/curing the optical material composition of the present invention to obtain an optical material. The composition of the present invention may be a polymerizable/curable composition containing the optical material composition and a polymerization catalyst. As the polymerization catalyst, amine, phosphine or an onium salt may be used, where it is particularly an onium salt, preferably a quaternary ammonium salt, a quaternary phosphonium salt, a tertiary sulfonium salt or a secondary iodonium salt, more preferably a quaternary ammonium salt or a quaternary phosphonium salt that has good compatibility with the optical material composition, and still more preferably a quaternary phosphonium salt. More preferable examples of the polymerization catalyst include quaternary ammonium salts such as tetra-n-butylammonium bromide, triethylbenzylammonium chloride, cetyldimethylbenzylammonium chloride and 1-n-dodecylpyridium chloride and quaternary phosphonium salts such as tetra-n-butylphosphonium bromide and tetraphenylphosphonium bromide. Among them, the polymerization catalyst is more preferably tetra-n-butylammonium bromide, triethylbenzylammonium chloride or tetra-n-butylphosphonium bromide.

The amount of the polymerization catalyst added cannot simply be determined since it may vary depending on the components and the mixing ratio of the composition as well as the polymerizing/curing method, but it is usually 0.0001% by mass to 10% by mass, preferably 0.001% by mass to 5% by mass, more preferably 0.01% by mass to 1% by mass and most preferably 0.01% by mass to 0.5% by mass, provided that the total amount of the optical material composition is 100% by mass (amount without the polymerization catalyst). If the amount of the polymerization catalyst added is more than 10% by mass, polymerization may take place rapidly. On the other hand, if the amount of the polymerization catalyst added is less than 0.0001% by mass, the optical material composition may not be cured sufficiently and heat resistance may be poor.

Of course, an additive such as an ultraviolet absorber, a bluing agent or a pigment can be added to the optical material composition upon producing an optical material by the production method of the present invention so as to further enhance the utility of the resulting optical material.

Preferable examples of the ultraviolet absorber include benzotriazole-based compounds, where particularly preferable compounds are 2-(2-hydroxy-5-methylphenyl)-2H-benzotriazole, 5-chloro-2-(3,5-di-tert-butyl-2-hydroxyphenyl)-2H-benzotriazole, 2-(2-hydroxy-4-octylphenyl)-2H-benzotriazole, 2-(2-hydroxy-4-methoxy phenyl)-2H-benzotriazole, 2-(2-hydroxy-4-ethoxyphenyl)-2H-benzotriazole, 2-(2-hydroxy-4-butoxyphenyl)-2H-benzotriazole, 2-(2-hydroxy-4-octyloxyphenyl)-2H-benzotriazole and 2-(2-hydroxy-5-tert-octylphenyl)-2H-benzotriazole.

The added amount of the ultraviolet absorber is usually 0.01-5% by mass with respect to the total of 100% by mass of the optical material composition.

If necessary, a polymer modifier may be added upon polymerizing/curing the optical material composition for the purpose of extending the pot life, dispersing heat upon polymerization and else. Examples of the polymer modifier include halides in Groups 13-16 of the periodic table. Among them, halides of silicon, germanium, tin and antimony are preferable, and chlorides of germanium, tin and antimony having an alkyl group are more preferable. More preferable compounds are dibutyltin dichloride, butyltin trichloride, dioctyltin dichloride, octyltin trichloride, dibutyl dichlorogermanium, butyl trichlorogermanium, diphenyl dichlorogermanium, phenyl trichlorogermanium and triphenyl antimonydichloride, and the most preferable compound is dibutyltin dichloride. The polymer modifier may be used alone or two or more types of them may be used as a mixture.

The amount of the polymer modifier added is 0.0001-5.0% by mass, preferably 0.0005-3.0% by mass and more preferably 0.001-2.0% by mass, provided that the total amount of the optical material composition is 100% by mass. If the amount of the polymer modifier added is less than 0.0001% by mass, a sufficient period of pot life cannot be ensured for the resulting optical material and if the amount of the polymer modifier added is more than 5.0% by mass, the optical material composition cannot be cured sufficiently and heat resistance of the resulting optical material may be deteriorated.

The optical material composition or the polymerizable/curable composition obtained as described above is injected into a shaped frame such as a mold and polymerized to give an optical material.

In order to enhance the quality of the optical material of the present invention, impurities are preferably filtrated and removed with a filter or the like having a pore diameter of about 0.1-5 μm upon injecting the composition of the present invention into a mold.

A composition of the present invention is usually polymerized as follows. Specifically, curing time is usually 1-100 hours and curing temperature is usually −10° C.-140° C. Polymerization is carried out by a step of maintaining a predetermined polymerization temperature for a predetermined period of time, a step of raising the temperature at 0.1° C.-100° C./h, a step of lowering the temperature at 0.1° C.-100° C./h, or by a combination of these steps.

In addition, at the end of curing, the resulting optical material is preferably annealed at a temperature of 50-150° C. for about 10 minutes to 5 hours in order to eliminate distortion of the optical material of the present invention. If necessary, the resulting optical material may further be subjected to surface treatments such as dyeing, hard coating, impact resistant coating, antireflection, antifogging or the like.

The optical material of the present invention can favorably be used as an optical lens. Since the optical lens produced using the composition of the present invention is excellent in stability, hue, light resistance and transparency, it can be used and be extremely useful in the fields that conventionally use expensive high refractive index glass lenses such as a telescope, binoculars and a projector for television. If necessary, it is preferably used in a shape of an aspherical lens. Since an aspherical lens is capable of making the spherical aberration to be substantially zero with a single lens, there is no need of eliminating spherical aberration with a combination of a plurality of spherical lens, and thus reduction in weight and production cost can be realized. Accordingly, the aspherical lens is particularly useful, among optical lenses, as a lens for a camera.

EXAMPLES

Hereinafter, the content of the present invention will be described by way of examples and comparative examples, although the present invention should not be limited to the following examples.
1. Method for Evaluating Peeling Mark A defect of remaining peeling mark in each of the optical materials obtained in Examples and Comparative examples below was evaluated by the following methods.

The optical material composition was injected into a −10 D-lens mold made from two glass plates and tapes and having an edge thickness of 15 mm and a mold diameter of 75 mm to allow polymerization/curing according to the methods described in Examples. The resultant was left to cool down, removed from the mold and annealed at 110° C. for 60 minutes. Thereafter, the surface conditions were visually observed. A hundred lenses for each optical material composition were prepared, where they were evaluated as "A" when none of the lenses had a peeling mark, "B" when 1-10 lenses had peeling marks, and "C" when 10 or more of the lenses had peeling marks. "A" and "B" were considered to be acceptable.
2. Method for Evaluating Releasability Positive lenses having an edge thickness of 7 mm, a center thickness of 7.5 mm, a mold diameter of 70 mm and a base curve of 10.25 D were prepared according to the method described in Examples to evaluate releasability from the mold after the polymerization/curing. Those that could easily be released were evaluated as "A", those that could be released were evaluated as "B" and those that were difficult to be released were evaluated as "C". "A" and "B" were considered to be acceptable.
3. Method for Evaluating Viscosity Stability During Storage To the episulfide compound as the main component in the optical material composition, 2-chloromethyl-[1,4]oxathiepane-6-ol as a cyclic compound represented by Formula (1) of the present invention was added and maintained under a nitrogen atmosphere at 40° C. for a week to trace the viscosity variation. The compound was evaluated as "A" when the increase in the viscosity after the storage was less than 5 mPa·s, "B" when the increase in the viscosity after the storage was 5 or more but less than 10 mPa·s, and "C" when the increase in the viscosity after the storage was 10 mPa·s or more. "A" and "B" were considered to be acceptable.

Example 1: Production of
2-chloromethyl-[1,4]oxathiepane-6-ol 185 g (2.0 mol) of epichlorohydrin, 30 g of water, 5 g of methanol and 1.5 g of 32% aqueous sodium hydroxide solution were placed into a triple-neck eggplant-shaped flask equipped with a thermometer and a gas blowing tube, and stirred while blowing 35 g (1.0 mol) of hydrogen sulfide therein and maintaining the liquid temperature at 5-15° C., thereby obtaining 210 g (0.96 mol) of bis(3-chloro-2-hydroxypropyl)sulfide.

210 g (0.96 mol) of the resulting bis(3-chloro-2-hydroxypropyl)sulfide was dropped into a mixed solution of 200 g of 32% aqueous sodium hydroxide solution, 200 g of water and 600 g of methanol, while maintaining the reaction temperature at −15° C. Thereafter, the reaction solution was returned to room temperature, into which 490 g of 20% sulfuric acid was dropped. 1,000 g of toluene was further added for extraction. The resulting organic layer was washed with water and the solvent was distilled away. Subsequently, the composition was purified with an ODS column, thereby obtaining 5.4 g (0.03 mol) of 2-chloromethyl-[1,4]oxathiepane-6-ol as a cyclic compound represented by Formula (1).

$^1$H-NMR (CDCl$_3$): 1.3 ppm (1H), 2.0 ppm (1H), 2.6 ppm (4H), 3.4 ppm (1H), 3.5 ppm (4H), 3.8 ppm (1H)

$^{13}$C-NMR (CDCl$_3$): 35 ppm, 37 ppm, 49 ppm, 73 ppm, 74 ppm, 80 ppm

Examples 2-7

Bis(β-epithiopropyl)sulfide (hereinafter, "Compound a-1") as an episulfide compound represented by Formula (2) was mixed with 2-chloromethyl-[1,4]oxathiepane-6-ol (hereinafter, "Compound b") obtained in Example 1 as the cyclic compound represented by Formula (1) at amounts indicated in Table 1 to give 100% by mass. To this, 1.0% by mass of 2-(2-hydroxy-5-t-octylphenyl)-2H-benzotriazole as an ultraviolet absorber and 0.05% by mass of tetra-n-butylphosphonium bromide as a polymerization catalyst were added, and thoroughly mixed at 20° C. for homogenization. Subsequently, the resultant was degassed at a vacuum level of 1.3 kPa, filtrated with a 1-μm PTFE filter, and injected into a −10 D-lens mold and a positive lens mold with a base curve of 10.25 D. The temperature was maintained at 30° C. for 10 hours, raised to 100° C. by spending 10 hours, and finally maintained at 100° C. for an hour for polymerization/curing. After polymerization/curing, the lenses were removed from the molds to evaluate peeling and releasability. The evaluation results are shown in Table 1.

Examples 8 and 9

The same procedure as Example 2 was carried out to evaluate releasability and peeling except that bis(β-epithiopropyl)disulfide (hereinafter, "Compound a-2") was used as Compound a (compound represented by Formula (2)) and the mixing amounts were as indicated in Table 1. The evaluation results are shown in Table 1.

Comparative Examples 1 and 2

The same procedures as Examples 2 and 8 were carried out to evaluate releasability and peeling except that the type of Compound a and the amounts of Compound a (compound represented by Formula (2)) and Compound b (compound represented by Formula (1)) were as indicated in Table 1. The evaluation results are shown in Table 1.

TABLE 1

|  | Compound a: % by mass | Compound b % by mass | Evaluation of releasability | Evaluation of peeling |
|---|---|---|---|---|
| Example 2 | a-1: 99.8 | 0.2 | A | A |
| Example 3 | a-1: 99.5 | 0.5 | A | A |
| Example 4 | a-1: 98.4 | 1.6 | A | A |
| Example 5 | a-1: 95.5 | 4.5 | B | A |
| Example 6 | a-1: 93.0 | 7.0 | C | A |
| Example 7 | a-1: 90.0 | 10.0 | C | A |
| Example 8 | a-2: 99.8 | 0.2 | A | A |
| Example 9 | a-2: 98.4 | 1.6 | A | A |
| Comparative example 1 | a-1: 100.0 | 0.0 | A | C |
| Comparative example 2 | a-2: 100.0 | 0.0 | A | C |

Examples 10-14

Compound a (compound represented by Formula (2)) was mixed with Compound b (compound represented by Formula (1)) at amounts indicated in Table 2 to give 100% by mass. To this, 10% by mass of bis(2-mercaptoethyl)sulfide (hereinafter, "Compound c-1") and further 1.1% by mass of 2-(2-hydroxy-5-t-octylphenyl)-2H-benzotriazole as an ultraviolet absorber and 0.05% by mass of tetra-n-butylphosphonium bromide as a polymerization catalyst were added, and thoroughly mixed at 20° C. for homogenization. Subsequently, the resultant was degassed at a vacuum level of 1.3 kPa, then filtrated with a 1-μm PTFE filter, and injected into a −10 D-lens mold and a positive lens mold with a base curve of 10.25 D. The temperature was maintained at 30° C. for 10 hours, raised to 100° C. by spending 10 hours, and finally maintained at 100° C. for an hour for polymerization/curing. After polymerization/curing, the lenses were removed from the molds to evaluate peeling and releasability. The evaluation results are shown in Table 2.

Comparative Examples 3 and 4

The same procedure as Example 10 was carried out to evaluate peeling and releasability except that the mixing amounts of Compound a (compound represented by Formula (2)) and Compound b (compound represented by Formula (1)) were as indicated in Table 2. The evaluation results are shown in Table 2.

TABLE 2

|  | Compound a % by mass | Compound b % by mass | Evaluation of releasability | Evaluation of peeling |
|---|---|---|---|---|
| Example 10 | a-1: 99.6 | 0.4 | A | A |
| Example 11 | a-1: 98.0 | 2.0 | A | A |
| Example 12 | a-1: 95.5 | 4.5 | B | A |
| Example 13 | a-1: 92.0 | 8.0 | C | A |
| Example 14 | a-2: 99.5 | 0.5 | A | A |
| Comparative example 3 | a-1: 100.0 | 0.0 | A | C |
| Comparative example 4 | a-2: 100.0 | 0.0 | A | C |

Examples 15-18

Compound a-1 (compound represented by Formula (2)) was mixed with Compound b (compound represented by Formula (1)) at amounts indicated in Table 3 to give 100% by mass. To this, 6.0% by mass of Compound c-1 and 4.0% by mass of m-xylylene diisocyanate were added and mixed. To this, 1.1% by mass of 2-(2-hydroxy-5-t-octylphenyl)-2H-benzotriazole as an ultraviolet absorber, 0.1% by mass of tetra-n-butylphosphonium bromide as a polymerization catalyst and 0.01% by mass of ZELEC UN (from Stepan) as a mold release agent were added, stirred and mixed at a mixing temperature of 20° C. for an hour for homogenization. Subsequently, the resultant was degassed at 20° C. at a vacuum level of 1.3 kPa, then filtrated with a 1-μm PTFE filter, and injected into a −10 D-lens mold and a positive lens mold with a base curve of 10.25 D. The temperature was maintained at 30° C. for 10 hours, raised to 100° C. by spending 10 hours, and finally maintained at 100° C. for an hour for polymerization/curing. After polymerization/curing, the lenses were removed from the molds to evaluate peeling and releasability. The evaluation results are shown in Table 3.

Comparative Examples 5

The same procedure as Example 15 was carried out to evaluate peeling and releasability except that % by mass of Compound a-1 (compound represented by Formula (2)) and Compound b (compound represented by Formula (1)) were as indicated in Table 3. The results are shown in Table 3.

TABLE 3

|  | Compound a-1% by mass | Compound b % by mass | Evaluation of releasability | Evaluation of peeling |
|---|---|---|---|---|
| Example 15 | 99.6 | 0.4 | A | A |
| Example 16 | 98.0 | 2.0 | A | A |
| Example 17 | 95.6 | 4.4 | B | A |
| Example 18 | 93.0 | 7.0 | C | A |
| Comparative example 5 | 100.0 | 0.0 | A | C |

Examples 19-22

Compound a-1 (compound represented by Formula (2)) was mixed with Compound b (compound represented by Formula (1)) at amounts indicated in Table 4 to give 100% by mass. To this, 1.2% by mass of 2-(2-hydroxy-5-t-octyl-phenyl)-2H-benzotriazole as an ultraviolet absorber, 14% by mass of sulfur and 0.5% by mass of mercaptomethyl imidazole were added and preliminarily reacted at 60° C. Thereafter, the temperature was cooled to 20° C. and a mixture solution of 5% by mass of Compound c-1, 0.2% by mass of dibutyltin chloride and 0.03% by mass of triethylbenzylammonium chloride as a polymerization catalyst was added, mixed for homogenization and then degassed. Subsequently, the resultant was filtrated with a 1-nm PTFE filter and injected into a −10 D-lens mold and a positive lens mold with a base curve of 10.25 D. The temperature was maintained at 30° C. for 10 hours, raised to 100° C. by spending 10 hours, and finally maintained at 100° C. for an hour for polymerization/curing. After polymerization/curing, the lenses were removed from the molds to evaluate peeling and releasability. The evaluation results are shown in Table 4.

Comparative Example 6

The same procedure as Example 19 was carried out to evaluate peeling and releasability except that % by mass of Compound a-1 (compound represented by Formula (2)) and Compound b (compound represented by Formula (1)) were as indicated in Table 4. The results are shown in Table 4.

TABLE 4

| | Compound a-1% by mass | Compound b % by mass | Evaluation of releasability | Evaluation of peeling |
|---|---|---|---|---|
| Example 19 | 99.9 | 0.1 | B | A |
| Example 20 | 98.0 | 2.0 | B | A |
| Example 21 | 95.6 | 4.4 | B | A |
| Example 22 | 93.0 | 7.0 | C | A |
| Comparative example 6 | 100.0 | 0.0 | B | C |

Examples 23-27

Compound a (compound represented by Formula (2)) was mixed with Compound b (compound represented by Formula (1)) at amounts indicated in Table 5, and thoroughly mixed for homogenization. This mixture was stored under a nitrogen atmosphere at 40° C. for a week to evaluate viscosity stability during storage. The evaluation results are shown in Table 5.

Comparative Examples 7 and 8

The same procedure as Example 23 was carried out to evaluate viscosity stability after storage except that Compound a (compound represented by Formula (2)) and Compound b (compound represented by Formula (1)) were added at amounts indicated in Table 5. The evaluation results are shown in Table 5.

TABLE 5

| | Compound a % by mass | Compound b % by mass | Viscosity stability during storage |
|---|---|---|---|
| Example 23 | a-1: 99.95 | 0.05 | B |
| Example 24 | a-1: 99.5 | 0.5 | A |
| Example 25 | a-1: 97.0 | 3.0 | A |
| Example 26 | a-1: 93.0 | 7.0 | A |

TABLE 5-continued

| | Compound a % by mass | Compound b % by mass | Viscosity stability during storage |
|---|---|---|---|
| Example 27 | a-2: 99.5 | 0.5 | A |
| Comparative example 7 | a-1: 100 | 0.0 | C |
| Comparative example 8 | a-2: 100 | 0.0 | C |

The invention claimed is:

1. A cyclic compound represented by Formula (1) below:

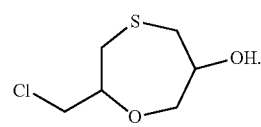

(1)

2. A composition for optical material comprising the cyclic compound represented by Formula (1) according to claim 1 and an episulfide compound represented by Formula (2) below:

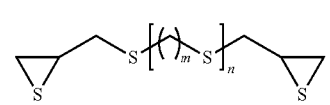

(2)

wherein m represents an integer of 0-4 and n represents an integer of 0-2.

3. The composition for optical material according to claim 2, wherein the amount of the cyclic compound represented by Formula (1) above is 0.001-5.0% by mass.

4. The composition for optical material according to claim 2, further comprising polythiol.

5. The composition for optical material according to claim 2, further comprising sulfur.

6. The composition for optical material according to claim 4, further comprising polyisocyanate.

7. A polymerizable and curable composition comprising the composition for optical material according to claim 2 and a polymerization catalyst in the amount of 0.0001% by mass to 10% by mass with respect to the total amount of the composition for optical material.

8. An optical material obtained by curing the composition for optical material according to claim 2.

9. An optical lens comprising the optical material according to claim 8.

10. A method for producing an optical material, comprising the steps of: adding a polymerization catalyst in the amount of 0.0001% by mass to 10% by mass with respect to the total amount of the composition for optical material according to claim 2; and polymerizing and curing the resultant.

11. The method for producing an optical material according to claim 10, further comprising a step of allowing partial polymerization of the episulfide compound represented by Formula (2) and sulfur, prior to the polymerizing and curing step.

12. An optical material obtained by curing the polymerizable and curable composition according to claim 7.

13. An optical lens comprising the optical material according to claim 12.

* * * * *